(12) United States Patent
Hiraoka et al.

(10) Patent No.: US 10,247,608 B2
(45) Date of Patent: Apr. 2, 2019

(54) SPECTROSCOPIC MODULE CONTROL METHOD

(71) Applicant: Panasonic Corporation, Osaka (JP)

(72) Inventors: Soichiro Hiraoka, Hyogo (JP); Masaya Nakatani, Hyogo (JP)

(73) Assignee: Panasonic Corporation, Osaka (JP)

( * ) Notice: Subject to any disclaimer, the term of this patent is extended or adjusted under 35 U.S.C. 154(b) by 10 days.

(21) Appl. No.: 15/559,435

(22) PCT Filed: Apr. 26, 2016

(86) PCT No.: PCT/JP2016/002191
§ 371 (c)(1),
(2) Date: Sep. 19, 2017

(87) PCT Pub. No.: WO2016/174865
PCT Pub. Date: Nov. 3, 2016

(65) Prior Publication Data
US 2018/0087964 A1    Mar. 29, 2018

(30) Foreign Application Priority Data
Apr. 28, 2015 (JP) ................. 2015-091930

(51) Int. Cl.
*G01J 3/45* (2006.01)
*G01J 3/26* (2006.01)
(Continued)

(52) U.S. Cl.
CPC .............. *G01J 3/26* (2013.01); *G01J 3/0202* (2013.01); *G01J 3/027* (2013.01); *G01J 3/0229* (2013.01);
(Continued)

(58) Field of Classification Search
CPC .......... G01J 3/26; G01J 3/0202; G01J 3/0229; G01J 3/0297; G01J 9/0246; G02B 26/001;
(Continued)

(56) References Cited

U.S. PATENT DOCUMENTS 5,387,974 A    2/1995 Nakatani

FOREIGN PATENT DOCUMENTS

| JP | 2-136722 | 5/1990 |
|----|----------|--------|
| JP | 5-248952 | 9/1993 |

(Continued)

OTHER PUBLICATIONS

International Search Report of PCT application No. PCT/JP2016/002191 dated Jul. 19, 2016.
(Continued)

*Primary Examiner* — Tarifur R Chowdhury
*Assistant Examiner* — Jonathon Cook
(74) *Attorney, Agent, or Firm* — McDermott Will & Emery LLP

(57) ABSTRACT

A method of controlling a spectroscopic module that includes a measurement light source, a variable-wavelength optical filter, a photodiode, and a conversion circuit for converting a drive signal voltage into a gap displacement amount. The spectroscopic module has a reference light source for emitting a reference light beam of a known wavelength. The controlling method involves varying a gap for the incident reference light beam, extracting two maximum points among data output from the photodiode, and updating a first conversion formula provided in the conversion circuit through use of drive signal voltages and gap amounts corresponding to the two points.

3 Claims, 2 Drawing Sheets

(51) Int. Cl.
    *G01N 21/01*       (2006.01)
    *G02B 26/00*       (2006.01)
    *G01J 3/02*        (2006.01)
    *G01J 3/10*        (2006.01)
    *G01J 3/12*        (2006.01)

(52) U.S. Cl.
    CPC ............. *G01N 21/01* (2013.01); *G02B 26/00* (2013.01); *G01J 2003/102* (2013.01); *G01J 2003/1273* (2013.01)

(58) Field of Classification Search
    CPC . G02B 5/284; G02B 6/29358; G01B 9/02072
    USPC .................................................. 356/451, 454
    See application file for complete search history.

(56) References Cited

FOREIGN PATENT DOCUMENTS

| | | |
|---|---|---|
| JP | 5-312646 | 11/1993 |
| JP | 2942654 B2 | 8/1999 |
| JP | 2015-031606 | 2/2015 |

OTHER PUBLICATIONS

The Extended European Search Report dated Apr. 13, 2018 for the related European Patent Application No. 16786142.6.

SPECTROSCOPIC MODULE CONTROL METHOD

This application is a U.S. national stage application of the PCT International Application No. PCT/JP2016/002191 filed on Apr. 26, 2016, which claims benefit of foreign priority of Japanese patent application 2015-091930 filed on Apr. 28,2015, respectively, the contents all of which are incorporated herein by reference.

FIELD OF THE INVENTION

The present invention relates to a method of controlling a spectroscopic module including a variable-wavelength optical filter that selectively transmits a beam of light of a predetermined wavelength by multiple reflection.

DESCRIPTION OF THE RELATED ART

A spectroscopic module of this kind generally has a known configuration in which a subject and a variable-wavelength optical filter are disposed in order between a measurement light source and a photodiode for light detection. The variable-wavelength optical filter has a known structure that utilizes a technology for transmitting light of a specific wavelength by means of interference resulting from multiple reflection of incident light between a pair of reflectors. The variable-wavelength optical filter makes a narrow gap formed between the pair of the reflectors undergo displacement and thereby changes the wavelength of transmitted light.

This spectroscopic module can be applied to multi-gas sensors that detect the type of gas by mid infrared radiation, and sensors that detect urine sugar or blood sugar levels by near infrared radiation, for example.

In the variable-wavelength optical filter as described above, the narrow gap formed between the pair of the reflectors is controlled by a drive method using any of electrostatic force, the inverse piezoelectric effect of a piezoelectric material, and a difference between thermal expansion coefficients of different materials.

The development of microelectromechanical system (MEMS) devices undergoing semiconductor fabrication processing is pursued to enhance the mass-producibility of variable-wavelength optical filters. The fabrication processing consists of designated dry etching and sputtering or photolithographic electrode forming performed on silicon- or other material-made semiconductor wafers. The wavelength reproducibility of variable-wavelength optical filters produced through this fabrication processing can be improved by restraining manufacturing variation or offsetting manufacturing variation through correction control.

However, the former method of restraining manufacturing variation involves very tight control of manufacturing processes and results in decreased yield. Thus, studies on the latter method of implementing correction control are pursued.

A conventional correction control method involves providing a reference light source for emitting a reference light beam of a known wavelength, dispersing the reference light beam by a variable-wavelength optical filter, detecting the dispersed beam by a photodiode, determining a difference between a wavelength of the detected beam and the known wavelength of the reference light beam, and adding a correction signal for offsetting the difference to a drive signal to correct a narrow gap between reflectors.

It should be noted that, for example, PTL 1 and PTL 2 are known as prior art documents containing information related to the invention in this application.

CITATION LIST

Patent Literature

PTL 1: Unexamined Japanese Patent Publication No. H02-136722

PTL 2: Unexamined Japanese Patent Publication No. H05-312646

SUMMARY OF THE INVENTION

It is an object of the present invention to ensure the productivity of spectroscopic modules and enhance the wavelength reproducibility of a spectroscopic module.

To accomplish this object, the present invention provides a method of controlling a spectroscopic module that includes a conversion circuit for converting drive signal voltages applied to a variable-wavelength optical filter into interference wavelength data. The spectroscopic module has a reference light source for emitting a reference light beam of a known wavelength. The controlling method involves varying a gap for the incident reference light beam, extracting two maximum points among data output from a photodiode, and updating a first conversion formula incorporated in the conversion circuit through use of drive signal voltages and gap amounts corresponding to the two points.

This configuration can ensure the productivity of spectroscopic modules and enhance the reproducibility of wavelengths detected with a spectroscopic module.

DETAILED DESCRIPTION OF THE PREFERRED EMBODIMENTS

Figure 4:
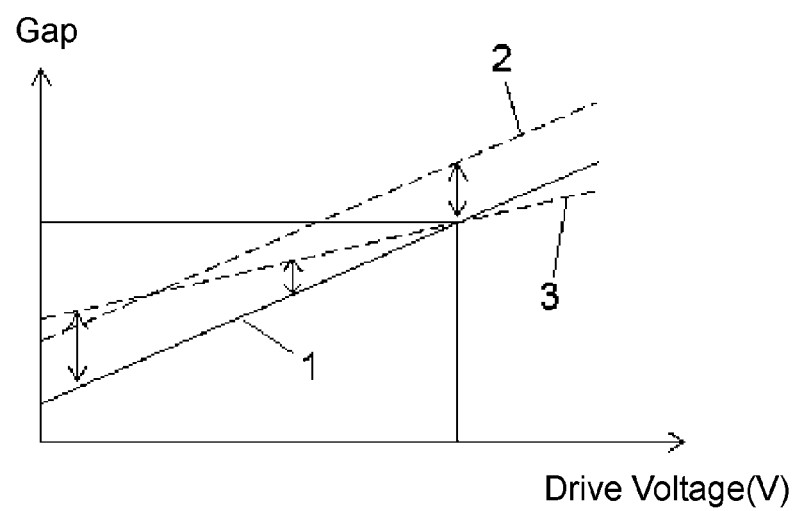
FIG. 4 is a graph showing a relationship between a gap provided in and drive voltage applied to the variable-wavelength optical filter of the spectroscopic module according to the exemplary embodiment of the present invention.

Prior to describing an exemplary embodiment of the present invention, problems in a conventional control method will briefly be described. A narrow gap is corrected by correcting a relationship between drive voltage applied to a variable-wavelength optical filter and the gap. If a piezoelectric drive method is employed, the relationship between the drive voltage and the gap is given by: $G=a \times V+b$, where G is the gap, a is a gap displacement amount per unit voltage, V is the drive voltage, and b is an initial gap. An initial characteristic of the relationship is shown by solid line 1 in FIG. 4. Correction to the narrow gap described above represents correction made to a translated initial characteristic shown by dashed line 2, i.e. correction made to the initial gap b.

However, correcting only the initial gap b leaves the gap displacement a per unit voltage uncorrected. This does not produce satisfactory correction effect. The gap displacement a is influenced by factors such as a change in substrate elasticity along with a temperature change, a change in resistance due to oxidizing electrode, and a change in the piezoelectric characteristic of a piezoelectric element. Because of variation in the proportional slope of a straight line shown by dashed line 3, correction is substantially inadequate in a region of wavelengths that greatly differ from a known wavelength.

This disadvantageously causes difficulty in offsetting the manufacturing variation described above and enhancing the reproducibility of wavelengths detected with a spectroscopic module.

Figure 1:
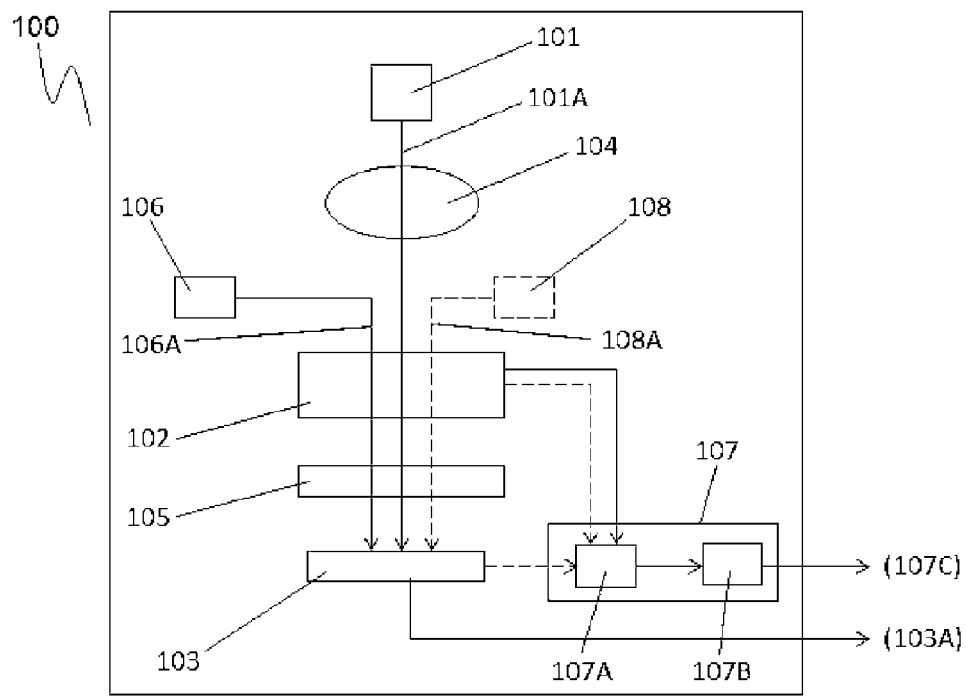
FIG. 1 is a schematic view of a spectroscopic module according to an exemplary embodiment of the present invention.

An exemplary embodiment of the present invention will now be described with reference to the attached drawings. FIG. 1 is a schematic view of spectroscopic module 100. Spectroscopic module 100 includes measurement light source 101, variable-wavelength optical filter 102, and photodiode 103 disposed in order. Subject 104 is disposed between measurement light source 101 and variable-wavelength optical filter 102. In spectroscopic module 100, measurement light source 101 emits measurement light beam 101A. Measurement light beam 101A is transmitted through subject 104, and variable-wavelength optical filter 102 disperses transmitted measurement light beam 101A by multiple reflection. Photodiode 103 detects dispersed measurement light beam 101A. Spectroscopic module 100 outputs signal strength data 103A from photodiode 103 and interference wavelength data 107C from variable-wavelength optical filter 102 to generate spectrum data.

Figure 2:
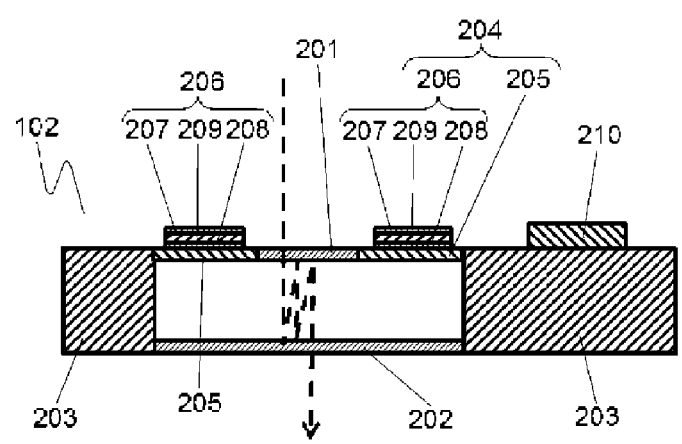
FIG. 2 is a cross-sectional view of a variable-wavelength optical filter included in the spectroscopic module according to the exemplary embodiment of the present invention.

Variable-wavelength optical filter 102 has a MEMS device structure incorporating semiconductor processing technology. FIG. 2 shows a basic structure of variable-wavelength optical filter 102. Variable-wavelength optical filter 102 includes a pair of opposed reflectors 201, 202 and frame 203 supporting a periphery of reflectors 201, 202. Upper reflector 201 is circular and has an outer edge that is connected to frame 203 via driver 204. Driver 204 includes rafter 205 that joins reflector 201 to frame 203 and drive layer 206 disposed on a top surface of rafter 205. Drive layer 206 includes upper electrode 207, piezoelectric film 209, and lower electrode 208 that are laminated in sequence.

Driver 204 applies a drive signal sent from control circuit 210 to upper electrode 207 and thereby causes a potential difference between upper and lower electrodes 207 and 208. As a result, a piezoelectric effect leads to bend of rafter 205 on which drive layer 206 is disposed. This enables reflector 201 connected to rafter 205 to move toward or away from the opposite reflector. In other words, a gap between the pair of reflectors 201, 202 can be flexibly adjusted by controlling drive signal voltage applied to drive layer 206 disposed above the reflectors.

After transmitted light passes through upper reflector 201, only a light beam of a wavelength that meets an interference condition set by the gap between the pair of reflectors 201, 202 produces resonance. Variable-wavelength optical filter 102 allows only the light beam (interference light) of the resonant wavelength (interference wavelength) to pass through lower reflector 202 and thereby extracts the light beam. In other words, the wavelength of the extracted light beam is determined by the gap between the pair of reflectors 201, 202, and variable-wavelength optical filter 102 can select an interference wavelength by letting the gap undergo displacement. Thus, variable-wavelength optical filter 102 can successively vary the narrow gap to select desired wavelengths and measure light quantities for the selected wavelengths to detect a spectrum.

Specifically, if the spectroscopic module applies drive signals to drive layer 206 and regulates the gap between reflectors 201, 202 to a range from 350 nm to 1.5 µm inclusive, the module can extract a light beam of any wavelength in a near-infrared light range (700 nm to 3.0 µm inclusive) from incident light of various wavelengths in accordance with a first order interference condition. The module includes a combination of bandpass filter 105 that removes unnecessary wavelengths extracted under interference conditions for other orders and photodiode 103 having sensitivity to a desired wavelength range. Thus, the module having the simple parts configuration can output signals to measure a spectrum in response to a near-infrared light range.

Photodiode 103 detects interference light beams emitted from variable-wavelength optical filter 102 and outputs signal strength data 103A concerning the detected interference light beams on a time-series basis. Spectroscopic module 100 includes conversion circuit 107 for converting drive signal voltages applied to variable-wavelength optical filter 102 into interference wavelength data 107C.

Conversion circuit 107 has first conversion formula 107A for converting drive signal voltages into gap displacement data and second conversion formula 107B for converting gap displacement data into interference wavelength data. Conversion circuit 107 includes a control integrated circuit (IC) and a recorder, for example. The recorder records programs or computational algorithms regarded as first and second conversion formulas 107A and 17B. First conversion formula 107A is represented by: $G=a \times V+b$, where G is a displacement amount of the gap between the pair of reflectors 201, 202 of variable-wavelength optical filter 102, a is a gap displacement amount per unit voltage, V is a drive signal voltage, and b is an initial gap. Second conversion formula 107B is represented by: $\lambda=2 \times G/n$, where $\lambda$ is an interference wavelength, n is an interference order, and G is a gap displacement amount.

Spectroscopic module 100 outputs interference wavelength data 107C from conversion circuit 107 and signal strength data 103A in response to interference wavelength data 107C from photodiode 103.

Spectroscopic module 100 includes reference light source 106 to detect a state of rafter 205 vibration caused by application of drive signals. Reference light beam 106A emitted from reference light source 106 is incident on variable-wavelength optical filter 102. Spectroscopic module 100 detects spectral characteristics of the beams and updates first conversion formula 107A for converting drive signal voltages into gap displacement data. Updating first conversion formula 107A refers to rewriting coefficients of a program or computational algorithm formula stored on the recorder, for example. Reference light beam 106A emitted from reference light source 106 has a known single wavelength.

Figure 3:
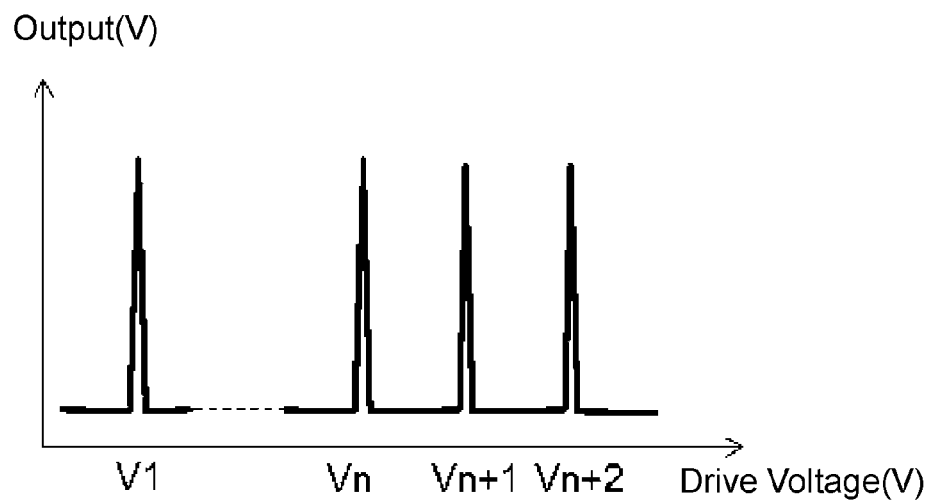
FIG. 3 is a graph showing a relationship between data output from a photodiode about a reference light beam dispersed by the variable-wavelength optical filter and drive voltages according to the exemplary embodiment of the present invention.

A method of updating first conversion formula 107A through use of reference light beam 106A will now be described. The method involves letting reference light beam 106A of a known single wavelength incident on variable-wavelength optical filter 102 and changing the drive signal voltage so as to vary the gap between reflectors 201, 202. As a result, reference light beam 106A (interference light beam) dispersed by variable-wavelength optical filter 102 is incident on photodiode 103. As shown in FIG. 3, a plurality of maximum points corresponding to interference orders of reference light beam 106A appear in response to drive voltages (V1 to Vn). The method further involves selecting two maximum points out of the plurality of these maximum points and determining drive voltages (Vn, Vn+1) for the respective detected maximum points as well as displacement amounts (Vn, GAPn), (Vn+1, GAPn+1) of the gap between reflectors 201, 202. GAPn and GAPn+1 are calculated using: G=λ×n/2, where λ is a wavelength of the reference beam and n is an interference order.

The gap displacement amount a per unit voltage and the initial gap b of the above-described equation G=a×V+b representing first conversion formula 107A are calculated from (V1, GAP1), (V2, GAP2) corresponding to the two interference orders. Thus, the spectroscopic module can update first conversion formula 107A of conversion circuit 107. This allows the module to make correction to the sloped initial characteristic shown by dashed line 3, as well as the translated initial characteristic shown by dashed line 2 in FIG. 4. Consequently, the module can control variable-wavelength optical filter 102 with high accuracy. In other words, an improvement in the wavelength reproducibility of spectroscopic module 100 contributes to offsetting the manufacturing variation of variable-wavelength optical filter 102 and ensuring the productivity of spectroscopic modules. This in turn enhances the reproducibility of wavelengths detected with spectroscopic module 100.

In the case of detecting a plurality of maximum points among data output from photodiode 103 as described above, the maximum points are linked to interference orders of reference light beam 106A. If the maximum points corresponding to discrete interference orders are extracted, the drive signal voltage changes in an increased range. In other words, the amount of rafter 205 bend increases, which causes problems such as degradation in the strength of rafter 205 and an increase in change duration. Consequently, it is preferable to extract maximum points corresponding to consecutive interference orders so that the drive signal voltage changes in a short range.

Maximum points may not be determined from different interference orders of reference light beam 106A. If the spectroscopic module further includes another light source 108 that emits reference light beam 108A of a wavelength different from the wavelength of reference light beam 106A, the module can detect consecutive maximum points spaced at intervals of a distance that is shorter than half the wavelength of reference light beam 106A dependent on consecutive interference orders. This configuration prevents degradation in rafter strength and an increase in change duration more effectively. Since reference light beam 106A has a different wavelength, interference occurs at varied gap sizes. This leads to definite gap absolute values.

The exemplary embodiment described above adopts a piezoelectric drive method in which driver 204 includes piezoelectric film 209, for example. Thus, the conversion formula is a linear equation having the drive voltage V as a variable, and can be updated using two maximum points output from photodiode 103. If the exemplary embodiment adopts an electrostatic force drive method, the conversion formula is a nonlinear equation represented by: G=a×V$^2$+bV+c, where a, b, and c each represent a constant. The constants a, b, and c of such a nonlinear equation can be determined by selecting three maximum points (V1, GAP1), (V2, GAP2), and (V3, GAP3) among data output from photodiode 103. In the case of adopting a piezoelectric drive method and selecting three maximum points, the module can have definite gap absolute values even if the interference orders are unknown.

Since spectroscopic module 100 disperses measurement light beam 101A emitted from measurement light source 101 and detects the dispersed light by photodiode 103, interference between measurement and reference light beams 101A and 106A results in a deterioration in the detection accuracy of spectroscopic module 100. Thus, it is preferred that measurement by measurement light source 101 and measurement by reference light source 106 be performed in a time division manner. The spectroscopic module alternates dispersing measurement light beam 101A and rewriting the conversion formula by reference light beam 106A, and thereby controls and corrects time-varying changes and temperature changes during measurement. This configuration enables the module to correct detected wavelengths with higher accuracy.

Preferably, first conversion formula 107A should be updated not only when the spectroscopic module starts detection but also in the middle of detection processes. This enables the module to make highly accurate correction even if a subject to be measured exhibits a specific absorption or reflection property near a known wavelength of reference light beam 106A.

The invention claimed is:

1. A method of controlling a spectroscopic module for dispersing a measurement light beam and detecting dispersed light, the spectroscopic module comprising:
   a measurement light source configured to emit the measurement light beam;
   a reference light source configured to emit a reference light beam of a known single wavelength;
   a variable-wavelength optical filter configured to output an interference light beam based on the measurement light beam or reference light beam by multiple reflection; and
   a photodiode configured to detect the interference light beam,
   wherein the variable-wavelength optical filter includes a pair of opposed reflectors and a driver that lets a gap between the pair of reflectors undergo displacement by receiving of a drive signal, and
   the spectroscopic module has a conversion circuit configured to convert a voltage of the drive signal into gap displacement data by a first conversion formula for a piezoelectric drive method and to convert the gap displacement data into data about an interference wavelength of the variable-wavelength optical filter by a second conversion formula for an interference of light, the method comprising:
   detecting two maximum points corresponding to orders of the interference light beam based on the reference light beam from the photodiode;
   updating the first conversion formula through use of results obtained from the two points;
   defining an absolute value of the gap; and
   alternating dispersing the measurement light beam and rewriting the first conversion formula by the reference light beam.

2. The method of controlling the spectroscopic module according to claim 1, comprising detecting two consecutive maximum points corresponding to orders of the interference light beam based on the reference light beam.

3. The method of controlling the spectroscopic module according to claim 2, further comprising:

detecting maximum points corresponding to consecutive orders of the interference light beam among data output from the photodiode; and updating the first conversion formula through use of results obtained from three maximum points corresponding to the consecutive orders of the interference light beam among data output from the photodiode.

\* \* \* \* \*